(12) United States Patent
Hsiao

(10) Patent No.: US 10,485,354 B2
(45) Date of Patent: Nov. 26, 2019

(54) ADJUSTMENT SYSTEM AND METHOD OF BED

(71) Applicant: Wen-Chang Hsiao, Taipei (TW)

(72) Inventor: Wen-Chang Hsiao, Taipei (TW)

( * ) Notice: Subject to any disclaimer, the term of this patent is extended or adjusted under 35 U.S.C. 154(b) by 44 days.

(21) Appl. No.: 16/008,105

(22) Filed: Jun. 14, 2018

(65) Prior Publication Data

US 2019/0038041 A1 Feb. 7, 2019

(30) Foreign Application Priority Data

Aug. 7, 2017 (TW) .............................. 106126523 A
May 18, 2018 (TW) .............................. 107206538 U

(51) Int. Cl.
| | |
|---|---|
| A47C 27/08 | (2006.01) |
| A47C 31/00 | (2006.01) |
| A47C 20/04 | (2006.01) |
| A47C 21/00 | (2006.01) |
| A47C 27/12 | (2006.01) |
| A61B 5/00 | (2006.01) |
| A61G 7/015 | (2006.01) |
| A61G 7/018 | (2006.01) |
| G08C 17/00 | (2006.01) |

(52) U.S. Cl.
CPC .......... *A47C 27/083* (2013.01); *A47C 20/048* (2013.01); *A47C 21/003* (2013.01); *A47C 27/128* (2013.01); *A47C 31/008* (2013.01); *A61B 5/4815* (2013.01); *A61G 7/015* (2013.01); *A61G 7/018* (2013.01); *G08C 17/00* (2013.01); *A61H 2201/0142* (2013.01); *A61H 2201/5097* (2013.01); *G08C 2201/32* (2013.01); *G08C 2201/93* (2013.01)

(58) Field of Classification Search
None
See application file for complete search history.

(56) References Cited

U.S. PATENT DOCUMENTS

| | | | | |
|---|---|---|---|---|
| 2013/0283530 | A1* | 10/2013 | Main ...................... | A47C 31/12 5/600 |
| 2018/0125256 | A1* | 5/2018 | Tsern ..................... | A47C 21/04 |

* cited by examiner

*Primary Examiner* — Sean Shechtman
(74) *Attorney, Agent, or Firm* — Bacon & Thomas, PLLC

(57) ABSTRACT

A system and a method for adjusting a bed are disclosed. The bed is preset with a plurality of sets of adjustment parameters. An external muscle strength/pressure detection device or method is used to select at least two sets of the adjustment parameters suitable for the user. The corresponding sleep parameters are detected when the user sleeps, and the user-specific adjustment parameters are quickly selected and sent back to the bed for adjustment. Through the method, there is no need for the bed to provide pressure sensors.

3 Claims, 6 Drawing Sheets

(A) pre-setting the adjustment parameters of the bed (B) selecting at least two sets of adjustment parameters suitable for the user (C) adjusting the hardness of the bed (D) detecting the sleep parameters (E) analyzing and obtaining the user-specific adjustment parameters (F) adjusting the bed according to the user-specific adjustment parameters

ADJUSTMENT SYSTEM AND METHOD OF BED

FIELD OF THE INVENTION

The present invention relates to an adjustment system and an adjustment method of a bed. The technical content relates to bed block adjustment, preset multiple sets of adjustment parameters, external muscle strength/pressure detection, and sleep state detection parameters. After comparing the parameters with each other, the adjustment parameters suitable for the user can be determined.

BACKGROUND OF THE INVENTION

In general, the bearing surface for the human body to lie down and sleep in the bed is composed of a single flexible material with elasticity. However, the user has different gravity centers (weights) of the various parts of the human body due to differences in body curve, height, and weight. Therefore, when the user sleeps in the bed, a single material bed surface will feedback different support forces in various parts of the body. This kind of situation that the body feedbacks different support forces tends to make the user unconsciously turn over and adjust the sleeping position during sleep, so that the body muscles cannot be completely relaxed.

In order to overcome the above problems, the purpose of the independent cylinder mattress, memory pillow or latex mattress on the market is to provide a solution to the problem of uneven support. Wherein, the design of different hardness on the bed in response to the curves of various parts of the human body is also one of the effective solutions to allow the bed surface to support evenly.

At present, various parts of the bed are designed to have different hardness or shape. Most of which uses air bed structures for medical use. A remote controller is used to manually control the inflation or deflation of multiple air bags arranged in the bed surface, so that each air bag can adjust its saturation. When the user lies in the bed, the difference in the saturation of each air bag produces different hardness.

Theoretically, although the above-mentioned air bed can provide more uniform support force, in practice, because the adjustment requires the user to lie down in the bed first while waking up and gradually adjust the bed according to his/her feelings, the process may cause the muscles to be unable to fully relax due to the natural reaction of the user's physical functions. Therefore, even if it is adjusted to the extent that the user thinks it is most comfortable, whether it can actually achieve the goal still requires the actual observation of the sleep situation.

In addition, even if the user adjusts the bed in his/her home to the state that he/she feels most comfortable, when going on a business trip or traveling, he/she often cannot get enough rest because he/she is not comfortable with the hardness of the bed in the hotel.

In the related art, US20160015184A1 discloses a pressure sensor on a bed to detect the pressure values of various parts of the user while sleeping in the bed, and separately detect the user's sleep state, such as Rapid Eye Movement (REM) state and deep sleep state, and then find out the pressure value in the preferred sleep state to adjust the bed.

However, the above method must provide the pressure sensor on the bed, which will increase the cost for the bed manufacturer. The pressure value and sleep state detected by the pressure sensor need a long period of time for comparison, statistics and analysis to find out the matching pressure value, and the efficiency is poor.

Accordingly, the inventor of the present invention has devoted himself based on his many years of practical experiences to solve these problems. Multiple sets of adjustment parameters are preset on the bed, and then at least two sets of the adjustment parameters are first selected by an external muscle strength/pressure detection device or method. The bed uses a sleep detection device to detect the user's sleep state under the conditions of the at least two sets of different adjustment parameters. The bed can more efficiently find the most suitable adjustment mode for the user without the need of a pressure senor. Besides, the parameters can be applied to all the beds with the same specification. When the user is away from home, as long as the bed has the same specification, it can be quickly adjusted through the user-specific adjustment parameters.

SUMMARY OF THE INVENTION

The primary object of the present invention is to provide an adjustment method and an adjustment system of a bed.

According to one aspect of the present invention, an adjustment method of a bed is provided. A bed surface of the bed is divided into a plurality of support blocks with an adjustable hardness according to different parts of a human body. The adjustment method comprises the following steps:
(A) setting the support blocks of the bed with different hardness combinations as multiple sets of different adjustment parameters;
(B) using an external muscle strength/pressure detection device or method to test a user, and selecting at least two sets of the multiple sets of adjustment parameters suitable for the user;
(C) adjusting the hardness of each of the support blocks of the bed according to the at least two sets of adjustment parameters selected in step (B);
(D) using a sleep detection module to detect sleep parameters of the user corresponding to the different adjustment parameters;
(E) using an analysis unit to obtain the different adjustment parameters and the sleep parameters of step (D), and analyzing the optimal sleep parameters and the corresponding adjustment parameters to form user-specific adjustment parameters; and
(F) retransmitting the user-specific adjustment parameters in step (E) to the bed or other beds with the same specification, so that the hardness of each of the support blocks of the bed can be adjusted according to the user-specific adjustment parameters.

According to another aspect of the present invention, an adjustment system of a bed is provided. The adjustment system comprises a bed, an external muscle strength/pressure detection device, a sleep detection module, and an analysis unit. The bed is divided into a plurality of support blocks. The bed is provided with an internal controller for adjusting the hardness of each of the support blocks. The internal controller is pre-arranged with multiple sets of different adjustment parameters according to different hardness combinations of the support blocks. The external muscle strength/pressure detection device can preselect at least two sets of the multiple sets of adjustment parameters for the user so that the internal controller of the bed can respectively adjust the hardness of each of the support blocks according to the at least two sets of adjustment parameters. The sleep detection module is able to detect the sleeping state of the user in the bed according to the different adjustment parameters and output sleep parameters to a cloud service platform. The analysis unit communicates with the internal controller and the sleep detection module through signals. The analysis unit compares and analyzes the different sleep parameters of the sleep detection module to find out the best sleep parameter and the corresponding adjustment parameters, so that user-specific adjustment parameters are formed and stored in an identification management unit. The internal controller of the bed adjusts the hardness of each of the support blocks according to the user-specific adjustment parameters stored by the identification management unit.

When implemented, the analysis unit can be set in the above-mentioned internal controller of the bed, or an external controller, or installed in a cloud service platform.

With the above method and system, the present invention can use an external muscle strength/pressure detection device or method to detect the user. In the multiple adjustment parameters of the bed, at least two sets of adjustment parameters suitable for the user are selected and the sleep state of the user is detected, thereby efficiently finding the optimal user-specific adjustment parameters. There is no need to provide pressure detection components on the bed. When the user goes on a business trip or travels in different locations, the other bed with the same specification can be quickly adjusted to the most comfortable state according to the user-specific adjustment parameters.

Embodiments of the present invention will now be described, by way of example only, with reference to the accompanying drawings.

DETAILED DESCRIPTION OF THE PREFERRED EMBODIMENTS

Figure 1:
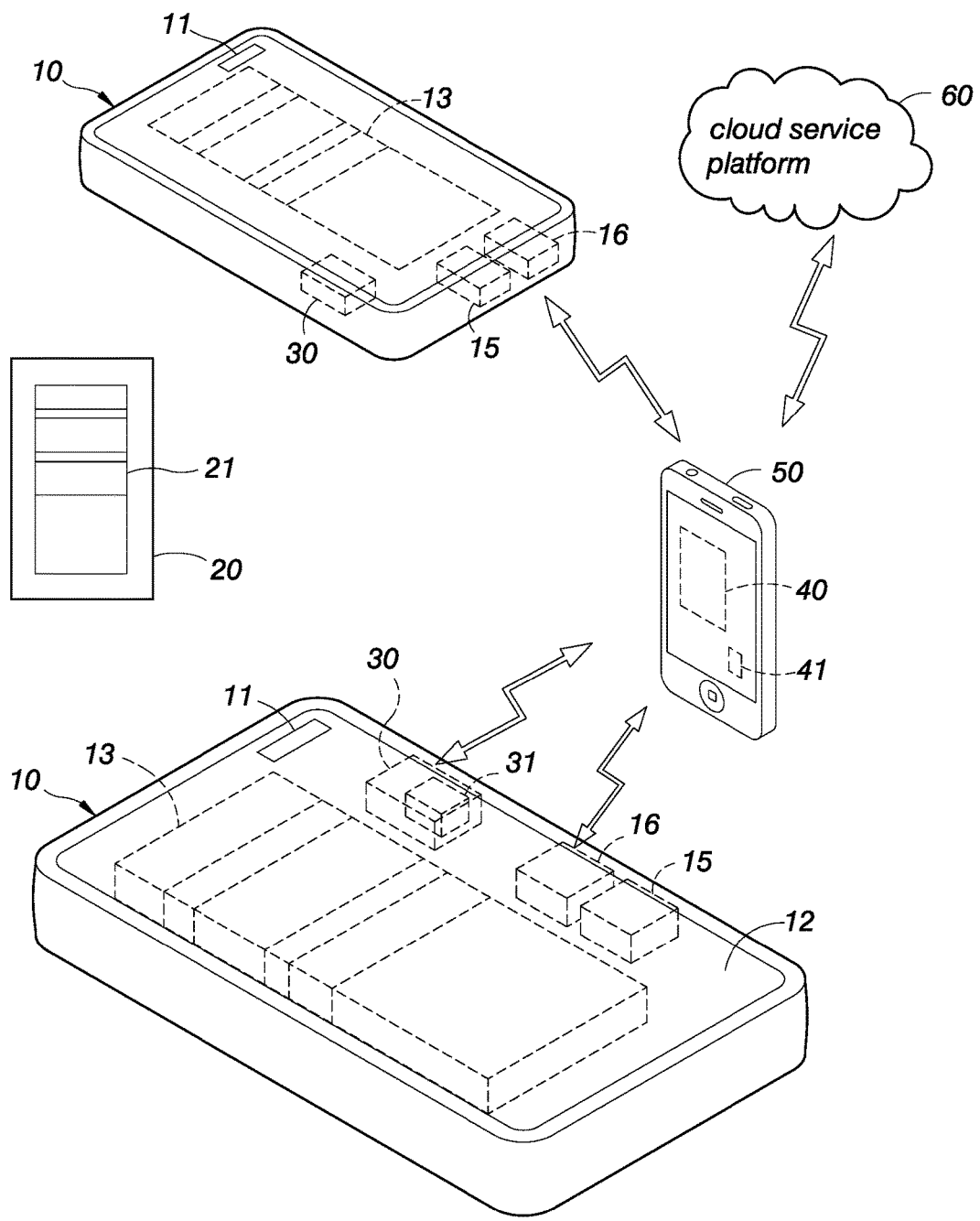
FIG. 1 is a first schematic view of an adjustment system in accordance with a first embodiment of the present invention.
Figure 2:
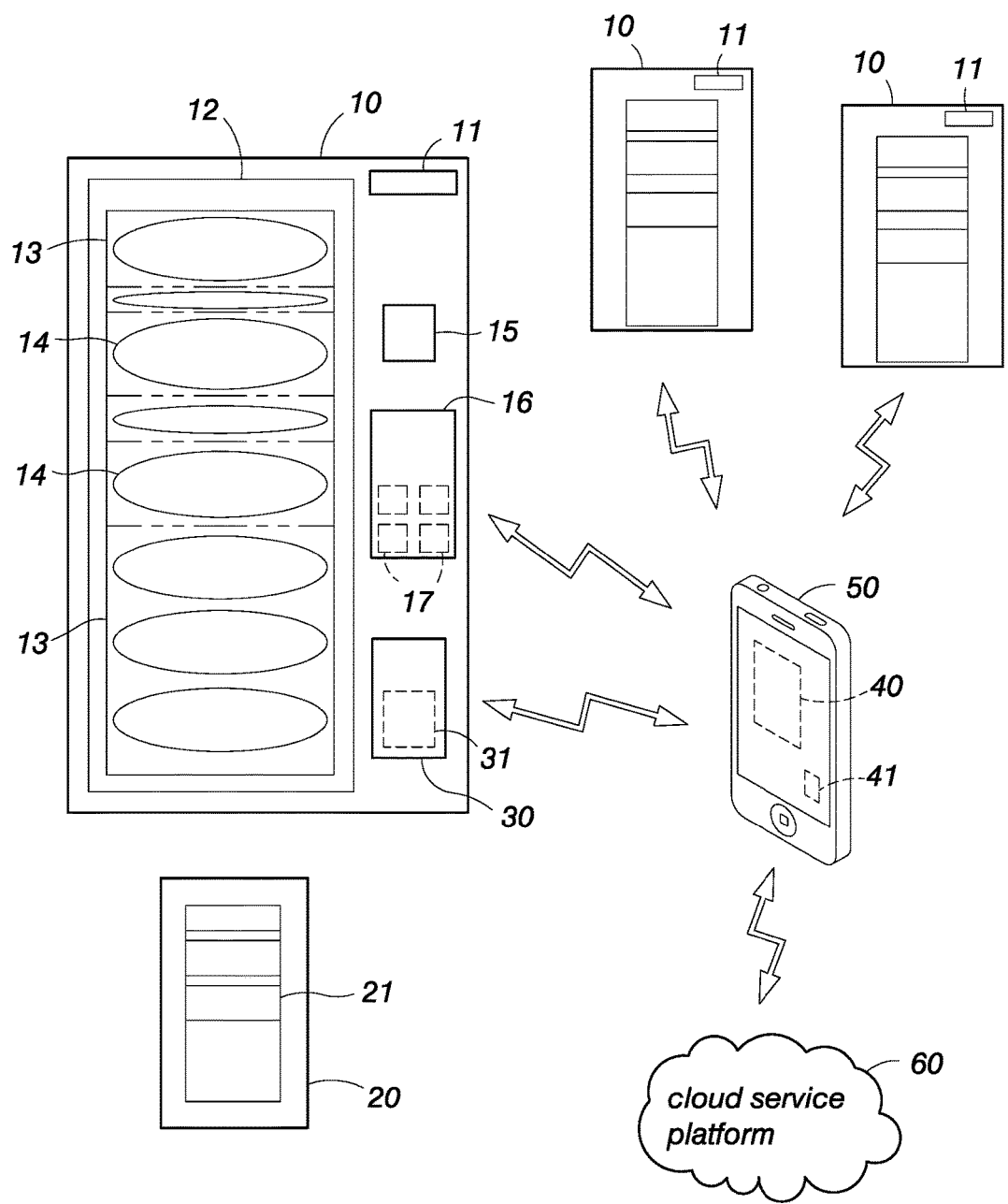
FIG. 2 is a second schematic view of an adjustment system in accordance with the first embodiment of the present invention.

As shown in FIG. 1 and FIG. 2, the present invention discloses an adjustment system of a bed 10. The bed 10 has an identification code unit 11 and a bed surface 12 that is divided into a plurality of support blocks 13 according to different parts of a human body. At least one air bag 14 is provided in each of the support blocks 13. The air bag 14 is connected to an inflation and deflation device 15. The inflation and deflation device 15 can adjust the hardness of the air bag 14 through an internal controller 16. The internal controller 16 is pre-arranged with multiple sets of different adjustment parameters 17 according to a combination of the different hardness of each of the support blocks 13.

For example, the support blocks 13 include a head block, a shoulder and neck block, a back block, a waist block, a buttock block, and a leg block. Each support block 13 has three adjustment modes, namely, soft, moderate and hard. When the adjustment parameters 17 are set, the head block is soft, the shoulder and neck block is moderate, the back block is soft, the waist block is hard, the buttock block is soft and the leg block is moderate to form a first set of adjustment parameters 17; the head block is moderate head, the shoulder and neck block is hard, the back block is soft, the waist block is soft, the buttock block is moderate and the leg block is hard to form a second set of adjustment parameters 17, and so on, to form the above-mentioned multiple sets of adjustment parameters 17.

In order to quickly find the adjustment parameters 17 that may be suitable for the user, the system may further include an external muscle strength/pressure detection device 20. When implemented, the external muscle strength/pressure detection device 20 includes a plurality of detection blocks 21 corresponding to the plurality of support blocks 13 of the bed 10. Each of the detection blocks 21 can detect the user by using a muscle strength or pressure detection method, and select at least two sets of the multiple sets of adjustment parameters 17 for the internal controller 16 of the bed 10 to respectively adjust the hardness of each air bag 14 according to the at least two sets of adjustment parameters 17. In practice, the external muscle strength/pressure detection method is not limited to the use of equipment. It may be the hardware, software, or manual test, as long as it can detect the muscle strength/pressure of the human body when sleeping.

Taking the aforementioned adjustment parameters 17 as an example, after detection, if the suitable adjustment parameters 17 of the user are the first set, the fourth set and the fifth set, when the first set of adjustment parameters 17 is selected by the internal controller 16, the internal controller 16 can adjust the plurality of support blocks 13, that is, the head block is soft, the shoulder and neck block is moderate, the back block is soft, the waist block is hard, the buttock block is soft, the leg block is moderate, and so on.

After the bed 10 is adjusted according to one set of the selected at least two sets of adjustment parameters 17, when the user sleeps in the bed 10, a sleep detection module 30 is used to detect the sleeping state of the user in the bed 10 and output a sleep parameter 31. Similarly, after the bed 10 is adjusted according to the other set of the selected at least two sets of adjustment parameters 17, the sleep detection module 30 outputs another sleep parameter 31 corresponding to the other set of adjustment parameters 17.

The sleep parameter 31 output by the sleep detection module 30 and the adjustment parameters 17 corresponding to the internal controller 16 are respectively transmitted to an analysis unit 40. The analysis unit 40 communicates with the sleep detection module 30 and the internal controller 16 through signals to compare and analyze the different sleep parameters 31 of the sleep detection module 30 to find out the best sleep parameter 31 and the corresponding adjustment parameters 17, so that the user-specific adjustment parameters 17 are formed and stored in an identification management unit 41. For example, the sleep parameter 31 includes physiological conditions such as brain waves, respirations, heartbeats, blood pressure changes, and eye movements when the user sleeps. The analysis unit 40 may determine the time when the user enters a deep sleep stage according to the changes of the physiological conditions. The longest period of deep sleep is the best sleep parameter 31.

After that, when the analysis unit 40 outputs the user-specific adjustment parameters 17 stored by the recognition management unit 41 in a wired or wireless manner, the internal controller 16 of the bed 10 adjusts the hardness of each support block 13 according to the user-specific adjustment parameters 17 to achieve the purpose of smart adjustment management of the bed after receiving the user-specific adjustment parameters 17.

It is worth mentioning that the analysis unit 40 may have a variety of possible implementation manners. As shown in FIG. 1 and FIG. 2, the analysis unit 40 is built in an external controller 50. In general, mobile devices, such as smart phones, smart watches or tablet computers that users carry with them, have data transmission capabilities. Therefore, the analysis unit 40 as shown in the figures may be in the form of application software (APP) installed and built in the external controller 50 composed of these mobile devices to facilitate user operation. Besides, these mobile devices may be used for the user to use text or voice input, fingerprint recognition or face recognition to log in and operate the analysis unit 40 to facilitate personal identification. Of course, the external controller 50 may be implemented with a physical device, for example, a drive-by-wire device or a remote controller, as long as it has data transmission capability and can be operated by the user.

Figure 3:
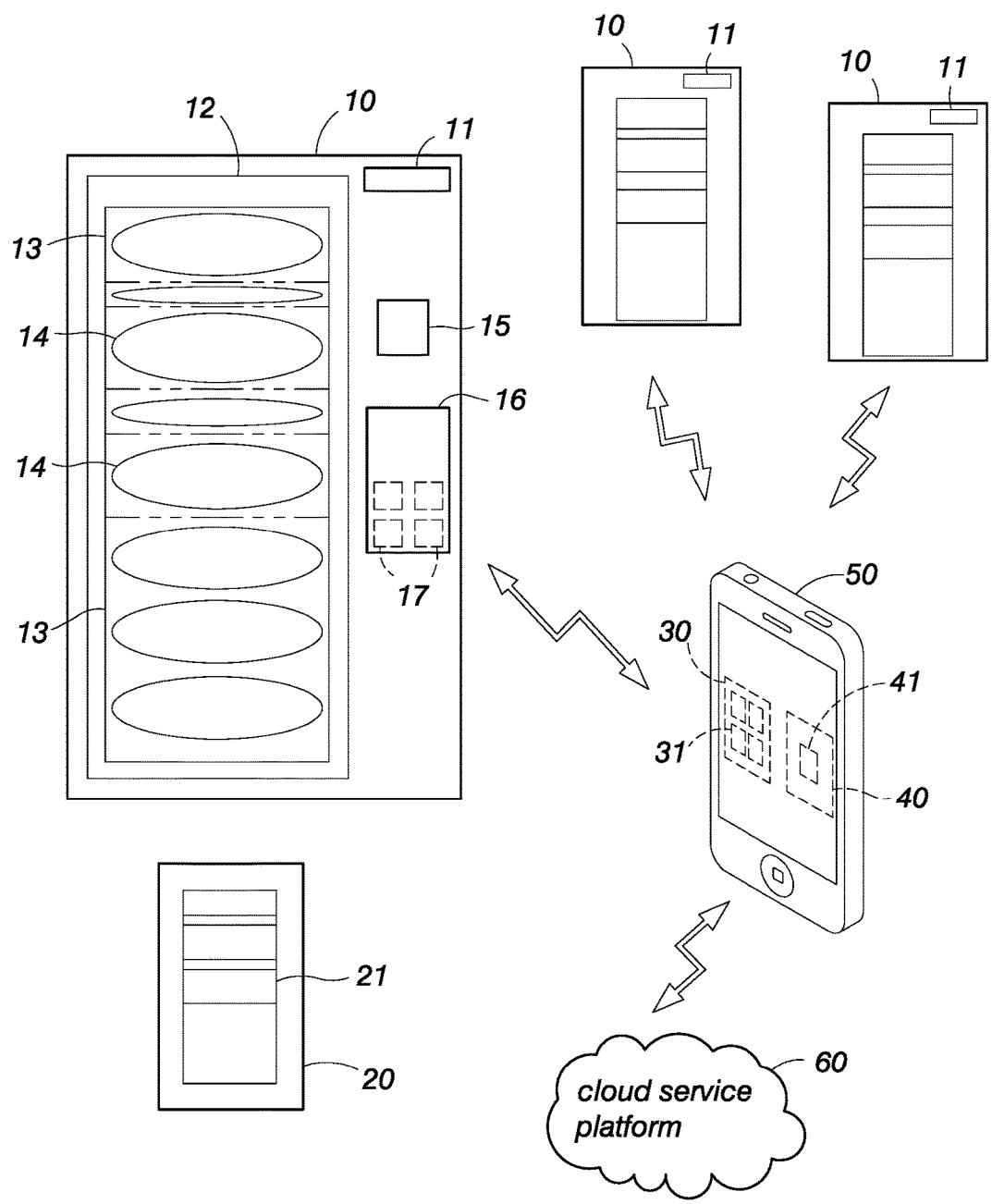
FIG. 3 is a schematic view of an adjustment system in accordance with a second embodiment of the present invention.

As shown in FIG. 3, in conjunction with the embodiment in which the analysis unit 40 is built in an external controller 50, the sleep detection module 30 in the form of application software (APP) may be installed and built in the external controller 50. When the user sleeps, the external controller 50 is placed on the side of the bed to analyze the aforementioned user-specific adjustment parameters.

Figure 4:
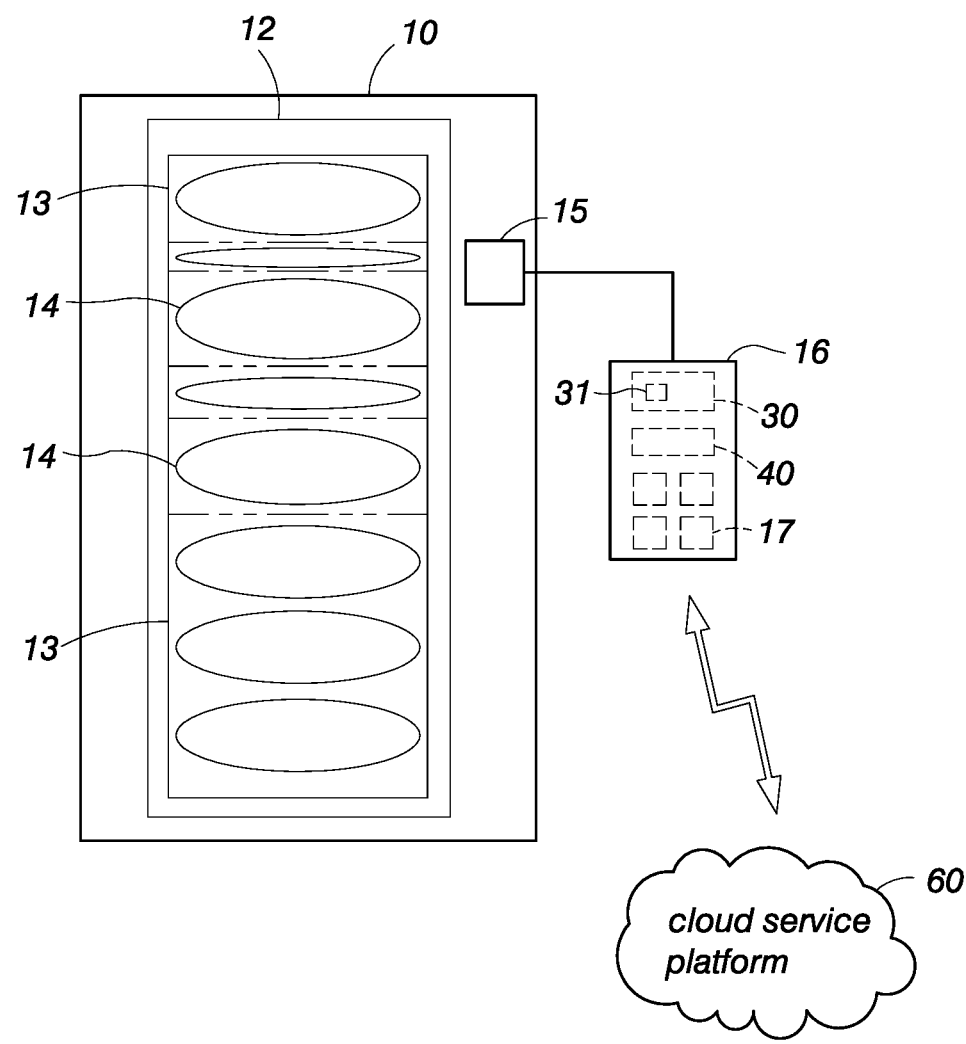
FIG. 4 is a schematic view of an adjustment system in accordance with a third embodiment of the present invention.

Alternatively, as shown in FIG. 4, both the analysis unit 40 and the sleep detection module 30 are built in the internal controller 16 of the bed 10. When the user finds out the best sleep parameter 31 and the corresponding adjustment parameters 17 by means of the above-mentioned method to form the user-specific adjustment parameters 17, it can be quickly adjusted to the optimal state for the user to sleep as long as the bed 10 is of the same specification.

In the embodiments shown in FIG. 1 to FIG. 4, no matter whether it is the internal controller 16 or the external controller 50, only a network interface (not shown) is required to upload the user-specific adjustment parameters 17 analyzed by the analysis unit 40 to a cloud service platform 60 for the management of the bed manufacturer or for users to download their own adjustment parameters at the remote site.

Figure 5:
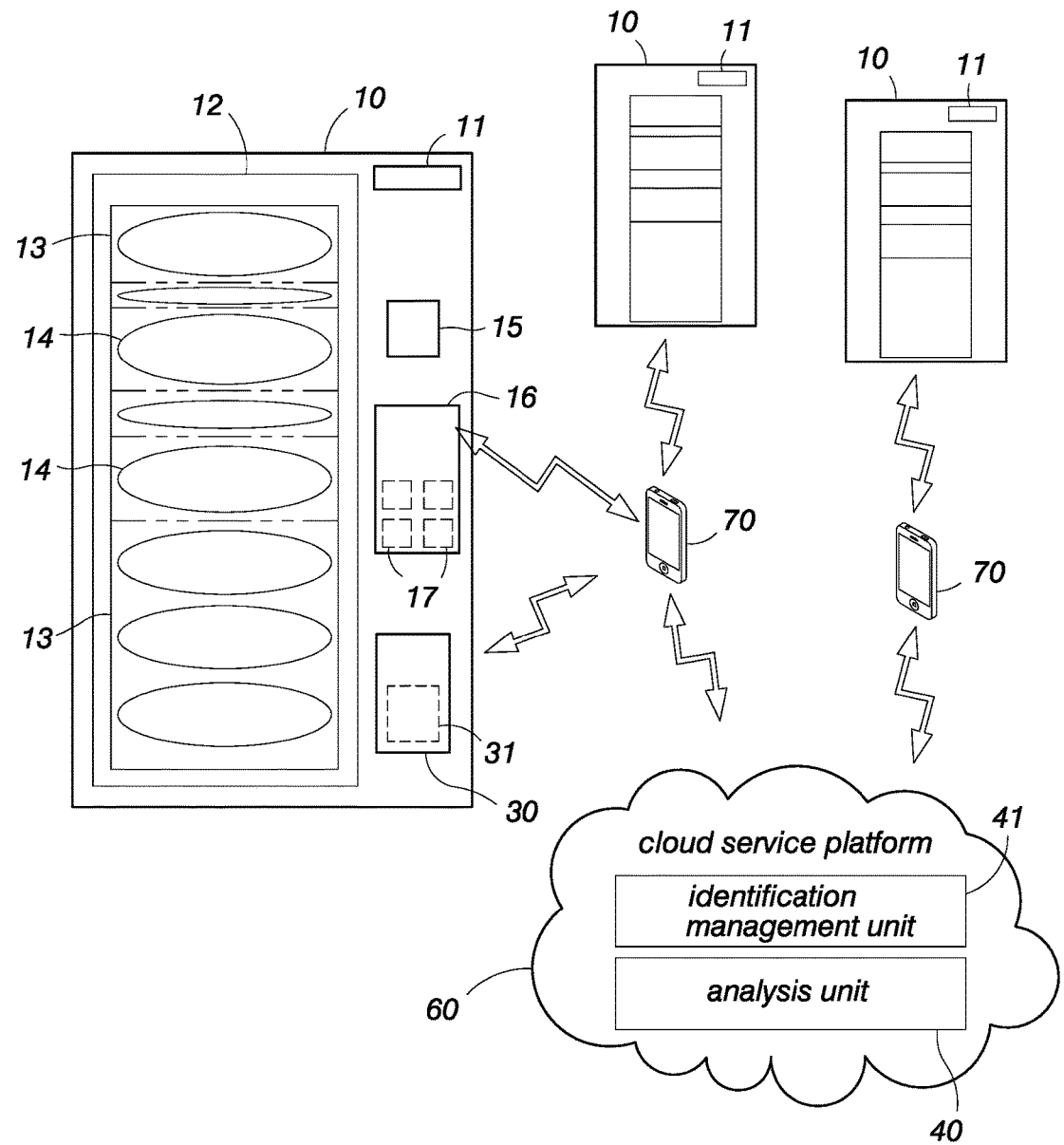
FIG. 5 is a schematic view of an adjustment system in accordance with a fourth embodiment of the present invention.

In addition, as shown in FIG. 5, the analysis unit 40 may be built in the cloud service platform 60 to analyze the trend of big data in the cloud. The embodiment further includes a network controller 70 communicated with the internal controller 16 and the sleep detection module 30 by means of signals, so that the adjustment parameters 17 of the internal controller 16 and the sleep parameter 31 detected by the sleep detection module 30 can be uploaded to the cloud service platform 60 through the network controller 70 for analysis by the analysis unit 40 built in the cloud service platform 60. The user-specific adjustment parameters 17 analyzed by the analysis unit 40 are transmitted to the internal controller 16 of the bed 10 through the network controller 70 for performing adjustment.

Figure 6:
FIG. 6 is a block diagram of an adjustment method of the present invention.
Figure 6:
Figure 6:
Figure 6:
Figure 6:

As shown in FIG. 6, according to the description of the above embodiment of the system, the method of the present invention comprises the following adjustment steps:

(A) pre-setting the adjustment parameters of the bed: the support blocks of the bed are combined into multiple sets of different adjustment parameters with different hardness;

(B) selecting at least two sets of the adjustment parameters suitable for the user: a particular user is tested by an external muscle strength/pressure detection device or method, and in the multiple sets of adjustment parameters of step (A), at least two sets of adjustment parameters suitable for the user are selected;

(C) adjusting the hardness of the bed: the hardness of each support block of the bed is adjusted according to the at least two sets of adjustment parameters selected in step (B);

(D) detecting the sleep parameters: when the specific user sleeps in the bed, a sleep detection module is used to detect the sleep parameters of the user corresponding to the different adjustment parameters;

(E) analyzing and obtaining the user-specific adjustment parameters: using an analysis unit to obtain the different adjustment parameters and the sleep parameters of step (D), and analyzing the optimal sleep parameters and the corresponding adjustment parameters to form the user-specific adjustment parameters; and (F) adjusting the bed according to the user-specific adjustment parameters: the user-specific adjustment parameters in step (E) are retransmitted to the bed or the other beds with the same specification, so that the hardness of each support block of the bed is adjusted according to the user-specific adjustment parameters.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. An adjustment method of a bed, a bed surface of the bed being divided into a plurality of support blocks with an adjustable hardness according to different parts of a human body, the adjustment method comprising the following steps:

(A) setting, by an internal controller of the bed, the support blocks of the bed with different hardness combinations as multiple sets of different adjustment parameters;

(B) using an external muscle strength/pressure detection device or method to test a user, and selecting at least two sets of the multiple sets of adjustment parameters for the user;

(C) adjusting the hardness of each of the support blocks of the bed according to the at least two sets of adjustment parameters selected in step (B);

(D) using a sleep detection module to detect sleep parameters of the user corresponding to the different adjustment parameters when the user sleeps in the bed in step (C);

(E) using an analysis unit to obtain the different adjustment parameters and the sleep parameters of step (D), and analyzing the optimal sleep parameters and the corresponding adjustment parameters to form user-specific adjustment parameters;

(F) retransmitting the user-specific adjustment parameters in step (E) to the bed or other beds with the same specification, so that the hardness of each of the support blocks of the bed can be adjusted according to the user-specific adjustment parameters;

(G) communicating with the internal controller and the sleep detection module by means of signals, by a network controller;
(H) uploading the adjustment parameters of the internal controller and the sleep parameters detected by the sleep detection module to a cloud service platform, which the analysis unit is built into, through the network controller; and
(I) transmitting, by the analysis unit of the cloud service platform, the user specific adjustment parameters to the internal controller of the bed, through the network controller, for performing adjustment, after the user-specific adjustment parameters are analyzed by the analysis unit of the cloud service platform.

2. An adjustment system of a bed, comprising:
the bed having an identification code unit, a bed surface of the bed being divided into a plurality of support blocks, the bed being provided with an internal controller for adjusting the hardness of each of the support blocks, the internal controller being pre-arranged with multiple sets of different adjustment parameters according to different hardness combinations of the support blocks;
an external muscle strength/pressure detection device, the external muscle strength/pressure detection device including a plurality of detection blocks corresponding to the plurality of support blocks of the bed to select at least two sets of the multiple sets of adjustment parameters for the internal controller of the bed to respectively adjust the hardness of each of the support blocks according to the at least two sets of adjustment parameters;
a sleep detection module, the sleep detection module being able to detect the sleeping state of the user in the bed according to the different adjustment parameters and output corresponding sleep parameters;
an analysis unit communicating with the internal controller and the sleep detection module through signals, the analysis unit comparing and analyzing the different sleep parameters of the sleep detection module to find out the best sleep parameter and the corresponding adjustment parameters, so that user-specific adjustment parameters are formed and stored in an identification management unit, the internal controller of the bed adjusting the hardness of each of the support blocks according to the user-specific adjustment parameters stored by the identification management unit;
a network controller communicating with the internal controller and the sleep detection module by means of signals;
wherein the analysis unit is built in a cloud service platform so that the adjustment parameters of the internal controller and the sleep parameters detected by the sleep detection module are uploaded to the cloud service platform through the network controller; and
wherein the analysis unit of the clouds service platform is configured to transmit the user-specific adjustment parameters to the internal controller of the bed through the network controller for performing adjustment, after the user-specific adjustment parameters are analyzed by the analysis unit of the cloud service platform.

3. The adjustment system of the bed as claimed in claim 2, wherein at least one air bag is provided in each of the support blocks, the air bag is connected to an inflation and deflation device controlled by the internal controller, so that the internal controller can control the saturation of the air bag to adjust the hardness of each of the support blocks through the inflation and deflation device.

\* \* \* \* \*